United States Patent
Hewett

(10) Patent No.: US 10,653,857 B2
(45) Date of Patent: May 19, 2020

(54) METHOD TO INCREASE QUALITY OF SLEEP WITH ACOUSTIC INTERVENTION

(71) Applicant: BrainFM, Inc., Chicago, IL (US)

(72) Inventor: Adam Hewett, Chicago, IL (US)

(73) Assignee: BrainFM, Inc., Chicago, IL (US)

(*) Notice: Subject to any disclaimer, the term of this patent is extended or adjusted under 35 U.S.C. 154(b) by 287 days.

(21) Appl. No.: 15/857,065

(22) Filed: Dec. 28, 2017

(65) Prior Publication Data

US 2019/0201658 A1    Jul. 4, 2019

(51) Int. Cl.

| | |
|---|---|
| *A61M 21/02* | (2006.01) |
| *H04S 7/00* | (2006.01) |
| *H04R 3/04* | (2006.01) |
| *H04R 3/12* | (2006.01) |
| *A61M 21/00* | (2006.01) |
| *H04R 3/00* | (2006.01) |
| *H04R 1/02* | (2006.01) |

(52) U.S. Cl.
CPC ............ *A61M 21/02* (2013.01); *H04R 3/04* (2013.01); *H04R 3/12* (2013.01); *H04S 7/30* (2013.01); *A61M 2021/0027* (2013.01); *H04R 1/028* (2013.01); *H04R 3/00* (2013.01); *H04S 7/302* (2013.01); *H04S 2400/11* (2013.01); *H04S 2420/01* (2013.01)

(58) Field of Classification Search
CPC .... H04R 3/12; H04R 3/04; A61M 2021/0027; A61M 21/02; H04S 7/30; H04S 2400/11
See application file for complete search history.

(56) References Cited

U.S. PATENT DOCUMENTS

2012/0251989 A1* 10/2012 Wetmore ............... G09B 19/00
                                                                                  434/236

* cited by examiner

*Primary Examiner* — Christine H Matthews
*Assistant Examiner* — Joshua Daryl D Lannu
(74) *Attorney, Agent, or Firm* — Lowenstein Sandler LLP

(57) ABSTRACT

A method for producing or modifying an audio composition to promote sleep and improve the quality of sleep. The invention provides a way to select for audio components which, when combined with modulated audio components, create an audio composition which has low salience and adequate variance to not just mask noise, but to encourage sleep without requiring repetitive, disruptive, or harmful audio elements.

17 Claims, 6 Drawing Sheets

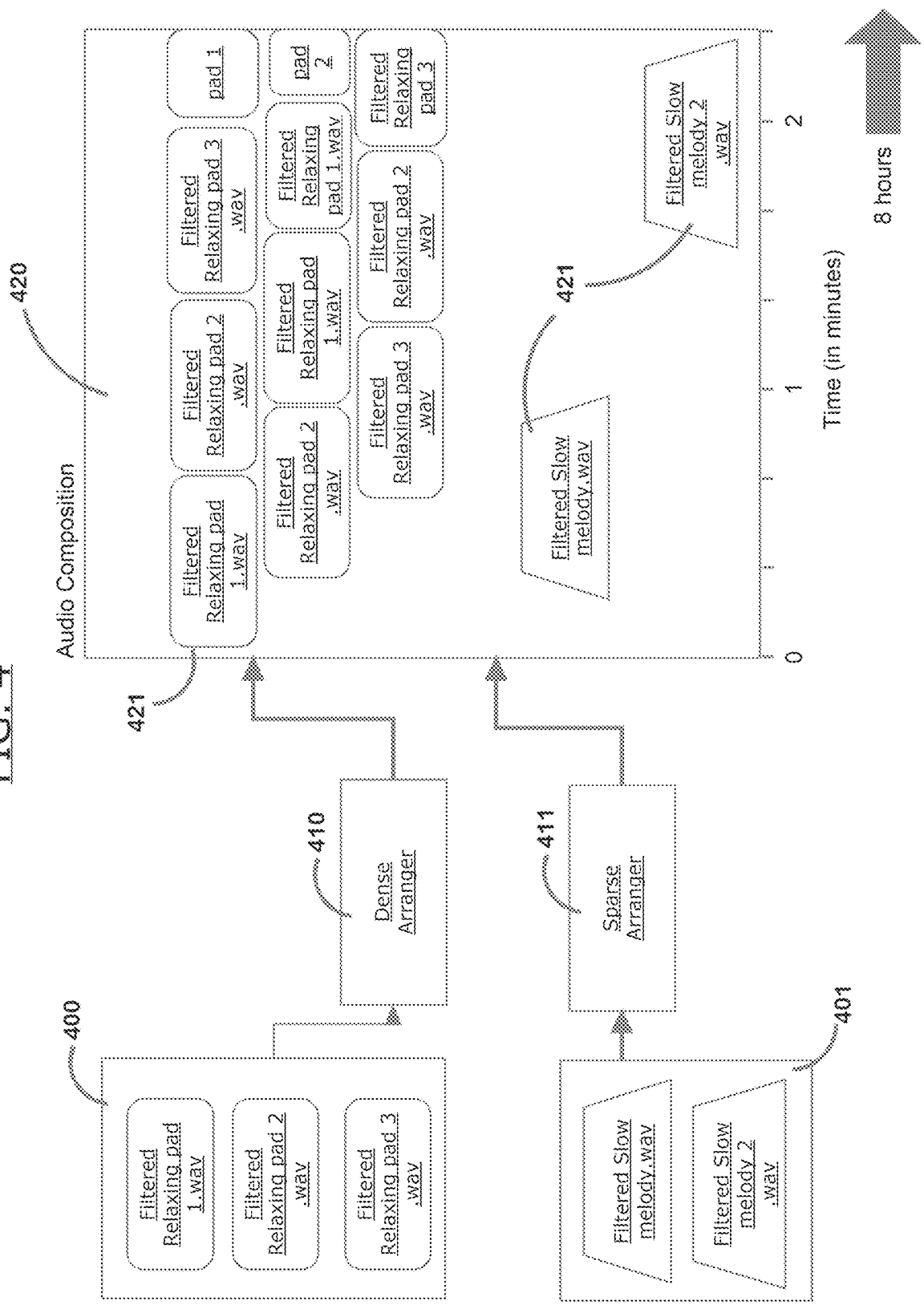

METHOD TO INCREASE QUALITY OF SLEEP WITH ACOUSTIC INTERVENTION

FIELD OF INVENTION

The present invention relates to a method of creating better audio to enhance sleep; more specifically, the invention relates to a method of creating or modifying an audio composition so that it assists in preventing sleep-onset insomnia and increases healthy brain activity during sleep.

BACKGROUND OF INVENTION

Poor sleep is an epidemic in the modern world. Sleep-onset insomnia—the inability to even get to sleep—is pervasive. Shallow sleep and frequent late-night awakenings are common, limiting access to arguably the most important stage of sleep called Slow-Wave Sleep, formerly defined as stages 3 and 4 of the sleep cycle. It is during this stage that memories are encoded from short term to long term, toxins such as beta-amyloids (linked to Alzheimer's) are flushed out, and is when chemicals like adenosine are flushed out, which is needed to feel fully rested and energetic the next day. Slow-Wave Sleep is characterized by very slow electrical brain wave oscillations from 0.1 hz to as high as 3 hz. It is the deepest stage of sleep and the hardest to reach.

One problem is that in even in the deepest stages of sleep, the brain is monitoring the audio of its surroundings intently for potential signs of danger. Unfortunately in the modern world this becomes a challenge to achieving healthy sleep, as the noises of everyday life have increased dramatically, even as the level of danger has decreased. This has led to problems getting to sleep, staying asleep, and in reaching that critical Slow-Wave Sleep Stage.

Previous inventions have used white noise to mask unwanted sounds, as shown by U.S. Pat. Nos. 9,694,154 and 8,019,092. However, white noise has been shown in laboratory experiments to be detrimental in some cases, as a more enriched sound environment supports healthy brain growth, even during sleep. White noise is often used as a control in sleep research because it is ineffective at truly enhancing sleep. Similarly, nature sounds like rain have been used, as shown by U.S. Pat. No. 7,749,155. But again, these sounds are often very white-noise-like and serve only to mask outside sound. In fact, some systems have endeavored to mask sounds entirely, as shown by U.S. Pat. No. 9,613,610. Still the problem remains—merely masking sound does not promote or enhance sleep. The fact is, if white noise, nature sounds, or any type of sound muffling or masking worked to alleviate the problem of insomnia, it would have done so a century ago.

Other previous inventions have attempted to use biofeedback devices to monitor sleep and present pleasant sounds, masking sounds, white noise, and other audio based on EEG or other physiological data, as shown by U.S. Pat. No. 7,041,049, U.S. Pat. App. Nos. 2013/338429, 2016/151602, and 2015/258301. Some have even targeted slow-wave sleep itself, as shown by U.S. Pat. App. No. 2017/304587. All of these inventions require the use of biofeedback of EEG devices, which are expensive, hard to manufacture, extremely invasive, and notoriously unreliable as consumer units. Furthermore, most suffer from much the same fundamental problems of other sound masking systems in that they use white noise or other masks.

Other large devices such as those that deliver vibroacoustic therapies as shown by U.S. Pat. App. No. 2010/179458, have additional limitations as well as the same invasiveness and large expense as biofeedback machines.

Other previous inventions have attempted to use traditional lullabies or other spoken-word methods like hypnosis, as shown by U.S. Pat. No. 9,415,184. While these may work for some people, for most adults they would be annoying and would only work for sleep-onset and not act to enhance sleep throughout the rest of the night.

Finally, previous inventions have endeavored to affect the electrical activity of the brain directly, this activity being called brain waves. One such method is call binaural beats, as shown by U.S. Pat. App. No. 2014/343354. However, binaural beats have been proven ineffective through scientific research. Binaural beats require frequencies in either ear that are inherently off-key, creating a stimulus that is boring, unchanging, or subliminal Other systems have used modulation of pleasing sounds as shown in U.S. Pat. No. 3,884,218, but rely on an EEG wave shape or target the wrong brain waves frequencies entirely as in U.S. Pat. No. 3,712,292. These systems also suffer from a lack of variance—they make only one kind of sound during the night. This is not only annoying and repetitive, but is also subject to what is called habituation, where the brain pays less and less attention to sounds that are always present, until they register barely any brain wave impression at all. There are other effective methods of affecting brain waves as shown in U.S. Pat. No. 7,674,224, but without salience, variance, and modulation patterns specifically adapted to sleep, these methods will not be effective.

SUMMARY OF INVENTION

The invention is summarized below only for purposes of introducing embodiments of the invention. The ultimate scope of the invention is to be limited only to the claims that follow the specification.

The present invention solves the described problems by creating or modifying an audio composition characterized by the following: 1) Audio that is low in salience. In other words, it is pleasant to listen to but easy to tune out. Such audio is typically not jolting or disruptive. 2) Audio that actively promotes slow-wave activity with modulations. 3) Audio that is adequate in variance. In other words, it enriches the audio environment instead of just masking it—making it helpful for sleep-onset, avoiding habituation during the night, and helping to train the user to sleep better on their own.

1) Low Salience

First and foremost, sleep music should be pleasant yet easy to tune out, so the user can withdraw into their own internal imaginings or peace, which helps with sleep-onset. It also can't jolt the listener awake due to an unexpected break or beat. It should be low in what is called salience, or how attention grabbing something is. The present invention provides a method to ensure low salience, even given the modulations involved and many complex modes of audio composition.

2) Promotes Slow-Wave Activity

The fact that the brain—even in deepest sleep—is always monitoring the audio environment makes sleep the perfect time for an acoustic intervention. EEG data has shown a remarkable response in the brain to slow modulations of audio, at frequencies ranging from 0.1-3 hz. The present invention provides a method to increase slow-wave activity from 10-30%, while leaving an otherwise healthy sleep profile. Sleep spindles—which indicate memories being encoded—also increased in-step proportionately to the rise in slow-wave activity induced through the method.

3) Adequate Variance

The present invention provides a method to ensure an engaging, pleasant auditory experience. One that can use music or even 3D audio to create an experience that helps dissociate the listener from their daily worries so they can fall asleep easily. The present invention also provides a method to vary the music and ensure novelty throughout the night, to reduce habituation, to keep the mind focused on the modulations, and to train the listener to sleep even in a highly enriched environment.

Use of the words "function" or "means" in the specification and claims is not intended to indicate a desire to invoke the special provision of 35 U.S.C. § 112, paragraph 6 to define the invention. To the contrary, if the provisions of 35 U.S.C. § 112, paragraph 6 are sought to be invoked to define the invention(s), the claims will specifically state the phrases "means for" or "step for" and a function, without also reciting in such phrases any structure, material, or act in support of the function. Moreover, even if the provisions of 35 U.S.C. § 112, paragraph 6 are invoked to define the inventions, it is intended that the inventions not be limited only to the specific structure, material or acts that are described in the embodiments, but in addition, include any and all structures, materials or acts that perform the claimed function, along with any and all known or later developed equivalent structures, materials, or acts for performing the claimed function.

Further objects and advantages of the present invention will become apparent from the consideration of the drawings and the following description. The description of the invention that follows, together with the accompanying drawings, should not be construed as limiting the invention to the example shown and described, because those skilled in the art to which this invention pertains will be able to devise other forms thereof within the ambit of the appended claims.

BRIEF DESCRIPTION OF DRAWINGS

FIG. 4—Depicts a flow chart of a software system that may be used to separate and arrange audio components according to a variance protocol.

DETAILED DESCRIPTIONS

Figure 1:
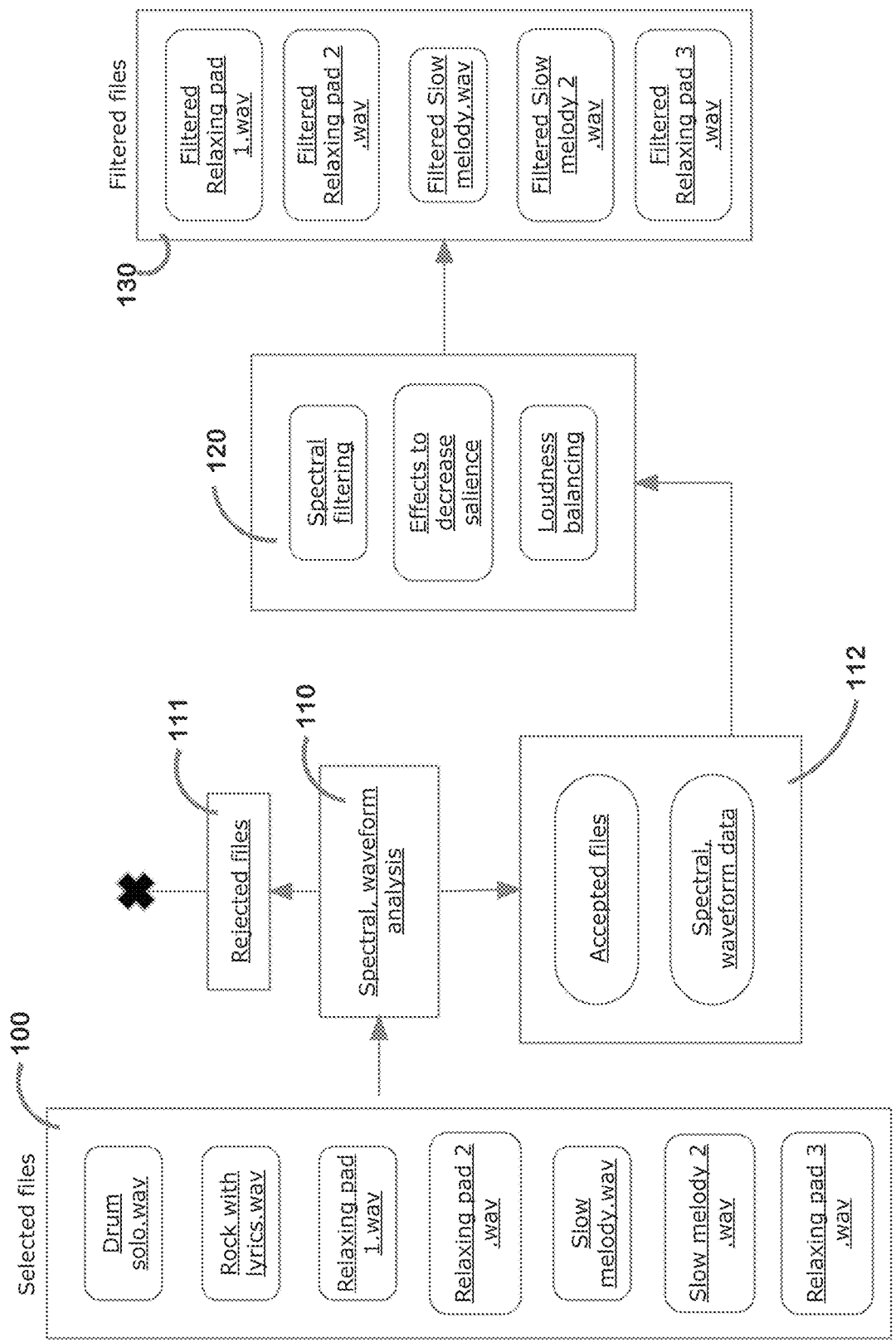
FIG. 1—Depicts a flow chart of a software system that may be used to separate, analyze, and modify audio components according to a salience protocol.

It is to be understood that the descriptions below are merely illustrative of several embodiments of the invention and that no limitations are intended to the detail of construction or design herein shown other than as defined in the appended claims.

These descriptions and drawings make use of the following definitions:

An "automatic arranger" is a conventional device or process that allows a user to define a number of audio components to fill an audio composition with music wherever the score has no implicit notes. The density or sparsity of an automatic arranger relates to the number of audio components used within the timeframe of the audio composition. An existing program capable of arranging is Mixtikl, sold commercially by Intermorphic.

A "band pass filter" is a conventional device or process that passes frequencies within a certain range and rejects frequencies outside that range. Software methods and code for this are readily available and should be well known by those versed in sound engineering. An existing program capable of band pass filtering is Adobe CS, sold commercially by Adobe Systems, Inc.

"Band stop filtering", also called a notch filter, t-notch filter, band-elimination filter, and band-rejection filter, is a conventional audio process that passes most frequencies unaltered, but attenuates those in a range to very low levels. Software methods and code for this are readily available and should be well known by those versed in sound engineering. An existing program capable of band stop filtering is Adobe CS, sold commercially by Adobe Systems, Inc.

An "equalizer" is a conventional device or process that adjusts the balance between frequency components, allowing the user to adjust the amplitude of audio signals at particular frequencies. An example program capable of equalizing is M/S Proc Mid/Side Level & EQ, sold commercially by ART Teknika, and an example equalizing device is dbx 215s Dual Channel 15-Band Equalizer, sold commercially by Harman.

"Low frequency oscillation" (LFO) is a technique where an additional oscillator that operates at a lower frequency modulates the audio signal, thus causing a difference to be heard in the signal without the actual introduction of another sound source. LFO is commonly used by electronic musicians to add vibrato or various effects to a melody. In this case it is used to modulate the amplitude, frequency, stereo panning or filters according to the modulation protocol selected. Software methods and code for implementing LFO are readily available and should be well known by those versed in sound engineering. An existing program capable of LFO is Omnisphere, sold commercially by Spectrasonics.

A "modular synthesizer" is a conventional device or process consisting of separate specialized modules, each being designed to allow the modification or processing of one parameter of an audio component, such as frequency (oscillator), spectrum (filter), or amplitude (amplifier). These modules are connected together through patch cords, a matrix patching system, or switches to create a patch. An example modular synthesizer program is Modular V, sold commercially by Arturia, and an example of modular synthesizer hardware is Moog System 55, sold commercially by Moog Music Inc.

A synth "pad" is a sustained chord or tone generated by a synthesizer, often employed for background harmony and atmosphere in much the same fashion that a string section is often used in orchestral music and film scores.

"Salience" means how attention-grabbing the audio is. For example, a car alarm is very attention grabbing and therefore high in salience. On the other hand, sounds that are pleasing and consistent have lower salience, such as a slow symphonic movement or the sound of wind and rain. Sudden changes are highly salient, such as a loud snap or the gunshot of a malfunctioning car muffler.

"Spatial audio" refers to any conventional technique or process of producing sound in which various sound elements seem to be at varying distances or directions from the listener. Spatial audio encompasses, for example, 3D audio, HRTF (Head-Related Transfer Function), surround sound, and other similar audio techniques used with headphones, speakers, and other sound producing devices.

"Spectral" profiles or analysis refers to sonographic representations and mathematical analysis of sound spectra, or by mathematically generated spectra. Spectral balancing focuses on manipulating the spectral features, interconnecting them, and transforming them. In this formulation, computer-based sound analysis and representations of audio signals are treated as being analogous to a timbral representation of sound. An example program capable of spectral analysis and balancing is iZotope RX, sold commercially by iZotope, Inc.

"Variance" means how the audio varies over time and incorporates novel elements. Low variance audio may consist of mere repetition or uniform sounds, while a very high variance audio may consist of erratic and continually changing audio components.

EXEMPLARY EMBODIMENTS

Since much sound modification and synthesis is now done on a computer, one embodiment of this invention is as a specially designed software program on a computer processor equipped with memory, interactive input (keyboard and mouse), audio input/output, speakers, and a conventional visual display. Optionally, the computer could interface with a sound synthesis device such as a keyboard or synthesizer, or could receive multiple inputs from a set of musical instruments via strategically placed microphones.

Selection of Sound Files

In this embodiment, selecting sound files for use in constructing the larger audio composition is the first step. FIG. 1 depicts the files selected by the user (100). In most cases a user would not have selected Drums or Rock or something with Lyrics for sleep. But even so, this embodiment of the salience protocol has the capability of compensating for that choice.

Salience Protocol

The primary goal of the salience protocol is to ensure that the constructed audio composition possesses low salience. "Low salience" means that all the selected audio components are similar in: loudness, spectral profile, complexity level, and adequacy for use in sleep. Low salience may be achieved by, for example, limiting unexpected transients; limiting high frequency sounds; smoothing any abrupt breaks in the sound; balancing the sound on one or more levels (including volume, loudness, spectral balancing, and complexity) so that audio is consistent; eliminating any annoying or repetitive sounds; ensuring that the internal melodic structure is free from disruptions such as pauses, breaks, or major volume deviations; using a smooth fade in/out, filtering to skew frequency content towards the lower end; changing the complexity level smoothly if it evolves over the timeline of the audio; using a consistent global melodic structure (that is, genre and melodies do not change or change slowly); filtering sounds like bells, crystal bowls, sitars, etc. to be less annoying, surprising, and grating; and not using lyrics.

FIG. 1 depicts a logical flow chart of the computer functions to be performed in accordance with one embodiment of the present invention. The computer programming starts with an input of two or more pre-composed audio files (100). Each file contains one or more audio components, so that together they are more complex than a sine wave. Alone or combined, they should ideally be rich, full-bodied musical pads or slow melodies. The files are put under waveform and spectral analysis (110) which can be used to detect transients, or spikes in the waveform usually indicating a drum beat. It can also be used to determine if a vocal track is present. This analysis can also look for consistency of the waveform and spectral profile across the entirety of the wave file, which would indicate a file most useful for sleep purposes. Some files might be rejected altogether (111) due to being incompatible with sleep audio. The accepted files along with their waveform and spectral data (112) are then sent through a series of filters (120), the purpose of which is to output new versions of the selected files (130) that are all the same in loudness and similar in spectral profile. The filters (120) would consist of band pass filters and equalizers to ensure a similar spectral profile—for example, a spectral profile that trends toward the lower end, as high pitched noises can be annoying. In addition, they would be subject to loudness balancing. Loudness is different than volume in that it uses a national standard algorithm to determine how loud the brain perceives sound to be, as opposed to looking at just the amplitude of the sound. Other effects may also be applied such as spectral repair, click reduction and cropping, if needed to achieve a batch of new files that are all of similar spectral, waveform qualities and loudness (130). Software to do perform these analyses and modifications already exists in programs such as iZotope RX, but this protocol could also be automated using batch processing techniques or programming.

Modulation Protocol

Slow-wave sleep brain wave oscillations rise 10-30% when audio is modulated at slow-wave frequencies, which range from 0.1 to 3 hz. The goal of the modulation protocol is to specify which frequencies will be used among the various audio components and when modulation will occur.

Figure 2A:
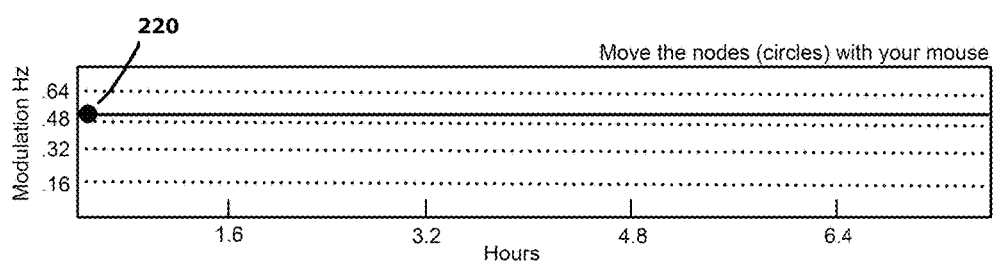
FIG. 2A—An example of a virtual display allowing for selection of a modulation protocol for one embodiment of the invention.
Figure 2B:
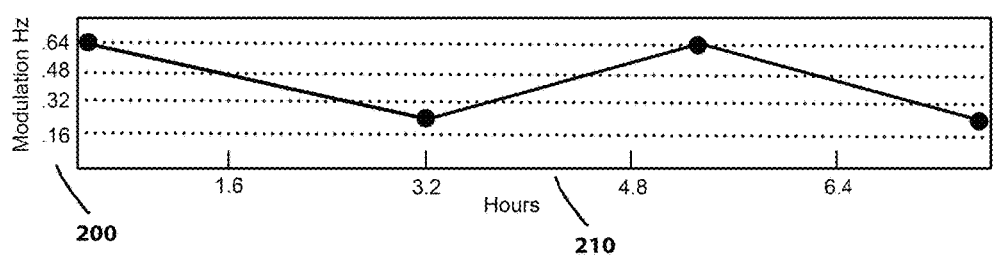
FIG. 2B—An example of a virtual display allowing for selection of a modulation protocol for one embodiment of the invention.
Figure 3A:
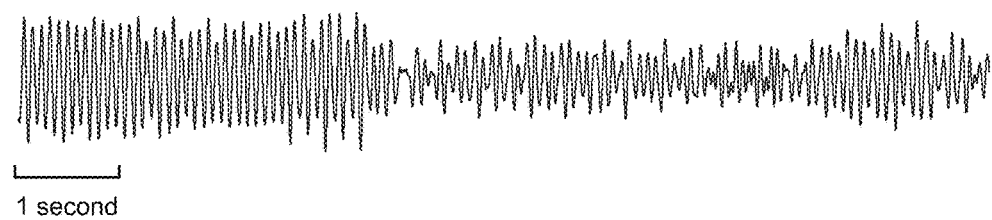
FIG. 3A—Depicts the wave form of an example audio component prior to modulation.
Figure 3B:
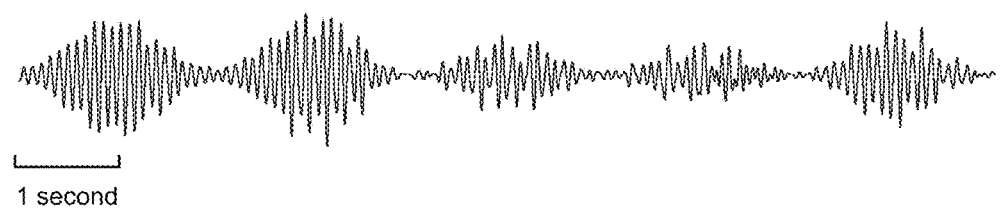
FIG. 3B—Depicts the wave form of an example audio component after modulation.

FIGS. 2A and 2B depict the one embodiment of a modulation protocol, where frequency of modulation (200) can be specified across the timeline of the audio composition by moving points (220) across a chart representing the timeline (210) with mouse input. In FIGS. 2A and 2B, the timeline of composition is assumed to be about 8 hours, represented horizontally (210) while the desired slow-wave frequency is represented vertically (200). FIG. 2A represents a simple protocol of straight 0.5 hz modulation across the entirety of the timeline. FIG. 2B represents a more complex protocol where slow-wave frequencies (200) are ramped and changed throughout the timeline. FIGS. 3A and 3B depict example results of applied modulation, for which in this embodiment is amplitude modulation applied to one or more filtered audio components using low-frequency oscillation. FIG. 3A depicts example audio components before modulation. FIG. 3B depicts example audio components after modulation, indicating a slow, regular pulsing sound that results from amplitude modulation.

Variance Protocol

The goals of the variance protocol are to ensure that the audio composition is continually changing, avoiding annoyingly repetition, but is also smooth and constant (limiting breaks in the audio). Variance can also be created by introducing novel stimuli to keep the brain from habituating. An example of a novel stimuli might be a relaxing instrument that is similar to the other instruments used but different enough to draw the brain's attention back in. An "adequate" level of variance is one high enough to prevent the brain from habituating and yet suitable for sleep. Adequate variance may be achieved by, for example, using audio with multiple frequency components (not just sine waves); change in the music over time; using audio that loops over a long timeline so as not to be noticeable or which does not loop; avoiding repetitive elements which may be annoying or attract too much attention; using audio which attracts attention at first (unlike white noise, for example), but which can be tuned out easily; and setting a protocol to introduce a number of novel stimuli periodically, including for example, a note which has not been used in a while, a relaxing sound, a new instrument, or a different type or number of instruments.

In one embodiment of the present invention, the action of the variance protocol is arranging the music. FIG. 4 depicts a logical flow chart of the computer functions to be performed in accordance with one embodiment of the present invention. The computer programming starts with an input of two or more pre-composed audio files (400) along with two or more additional pre-composed audio files (401). In the present embodiment, these files are the results of the salience and modulation protocols being applied as described above. In the case of the first set of files (400) they are sent to a dense automatic arranger (410) that distributes the files evenly (421) across the entirety of the audio composition (420). This ensures that there is always something playing, that the combined loudness remains constant, and that the files overlap with themselves as little as possible so as not to be annoying (421). The second set of files (401) are sent to a sparse automatic arranger (411) that distributes them sparingly (421) across the entirety of the audio composition (420). This ensures that there are pleasant surprises and novel stimuli strewn throughout the audio composition to reduce habituation and add to the overall pleasantness of the experience. In one embodiment, pad files (400) are used with the dense automatic arranger (410) and melody files (401) are used with the sparse automatic arranger (411).

Spatial Audio

In one embodiment, the final audio composition is played through earbuds or headphones, allowing for another powerful audio tool in the form of 3D audio. 3D audio is a spatial audio technique well established in the field and is also known to audio engineers as Head-Related Transfer Function (HRTF). HRTF makes it seem as if sounds are coming from a specific point in front, back, sides, or at any elevation. Moreover, these sounds can be made to seem as if they are moving. For the purposes of sleep, such an embodiment can make the sound very intriguing and help with sleep-onset. It can also help draw the mind to the stimulus, preventing habituation. Finally, it can help train the listener to ignore outside stimuli so as to train them to sleep better in the future. Alternative embodiments may use other techniques for making sounds seem to come from a specific point, such as surround sound speakers.

Figure 5A:
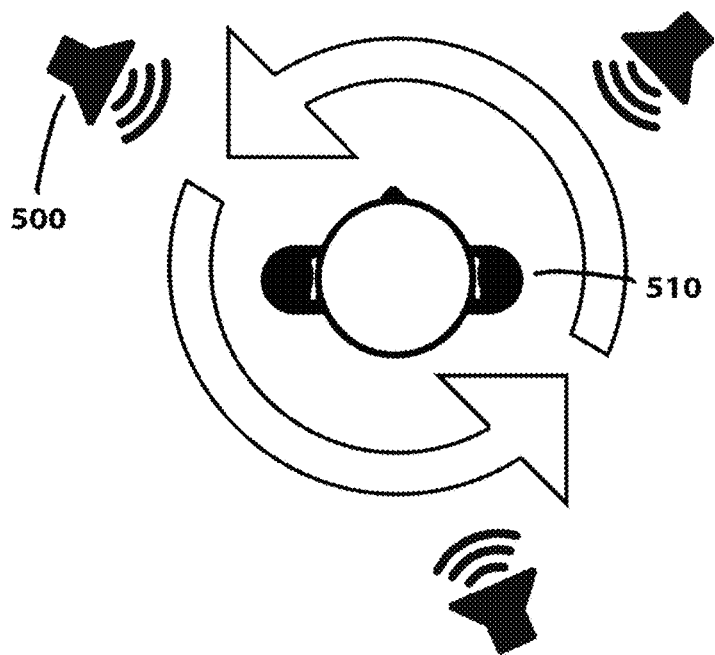
FIG. 5A—Depicts a representation of spatial audio components rotating around a listener.
Figure 5B:
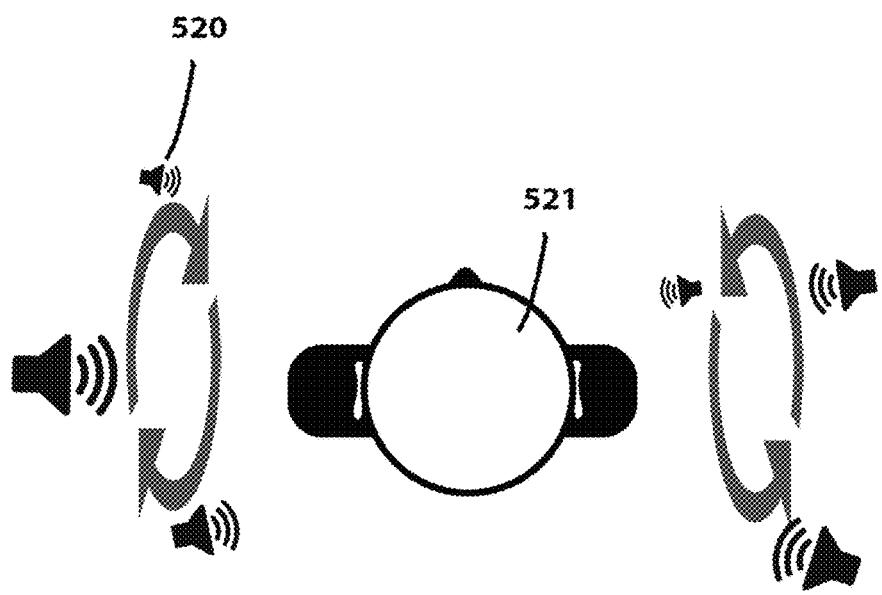
FIG. 5B—Depicts a representation of spatial audio components rotating around a Z axis on either side of a listener.

FIG. 5A depicts sounds (500) rotating around the head of a listener (510). The sounds (500) represent individual audio components being played from different 3D locations. In one embodiment the rotation would be very slow, at a rate of one to ten cycles per minute. The rotation cycle can also be timed with the modulation protocol and the frequency in cycles per second. FIG. 5B depicts a different type of rotation found to be effective, in which sounds (520) are rotated on the Z axis to either side of the listener (521).

Process Overview and Sound Mixing

Figure 6:
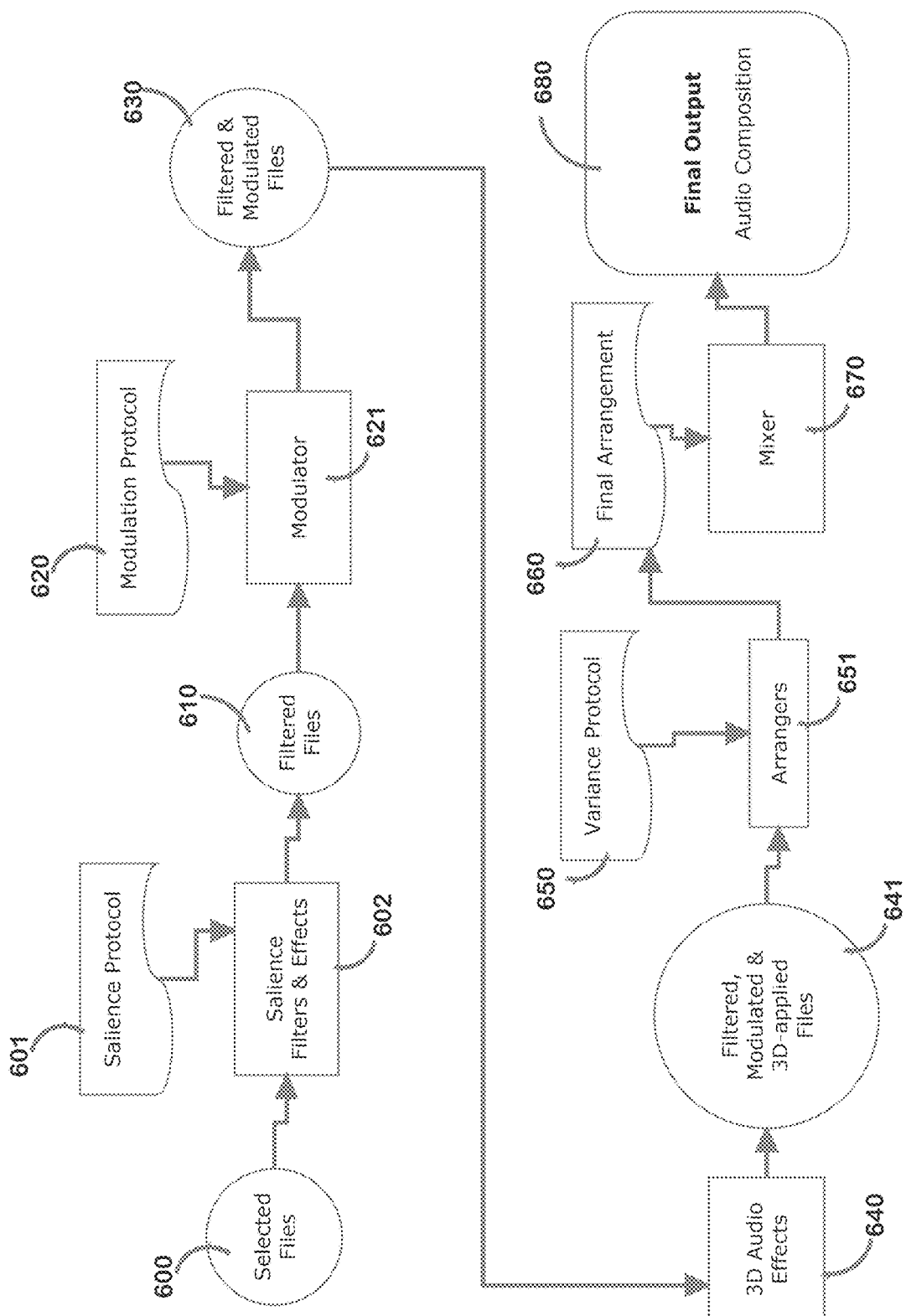
FIG. 6—Depicts a flow chart of a software system that may be used to apply a salience protocol, a modulation protocol, spatial audio effects, and a variance protocol to selected audio components and then mix modified components to output a final audio composition.

FIG. 6 depicts the overall process for an embodiment of the invention wherein the audio components (600) are processed (602) in accordance with the salience protocol (601). The filtered audio components are then sent to the modulator (621) that functions in accordance with the modulation protocol (620). 3D effects (640) are added to the filtered and modulated audio components (630). The audio components (641) are then arranged (651) according to the variance protocol (650) into a final arrangement (660) which is then sent to the mixer (670) to produce the final audio composition (680). In some embodiments, the final audio composition is stored on electronic medium and also may be electronically transmitted to a distant listener.

OTHER EMBODIMENTS

Figure 7:
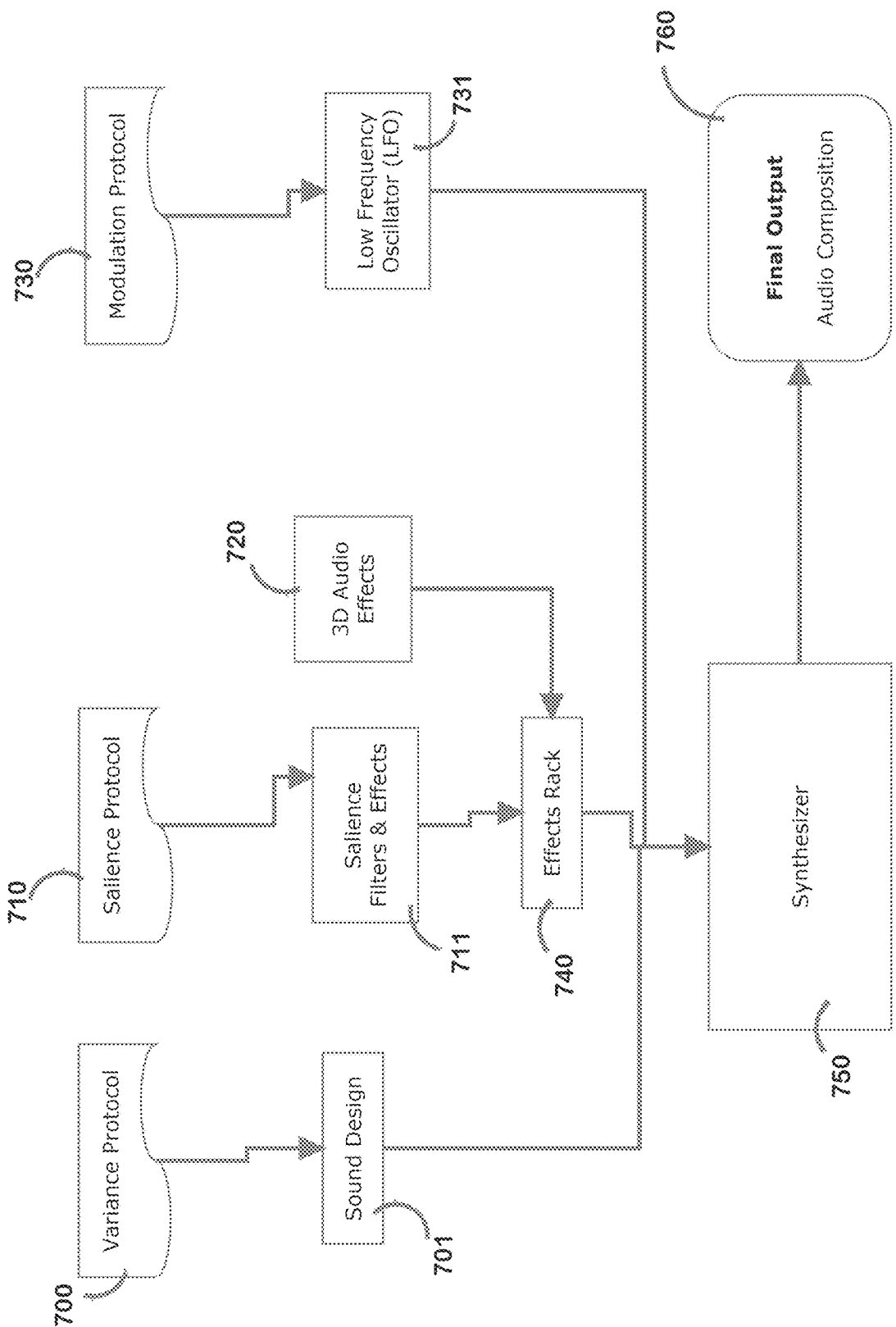
FIG. 7—Depicts a flow chart of an alternate hardware system that may be used to generated audio components, apply salience, modulation, and variance protocols, apply spatial audio effects, and output a final composition.

While the above description contains many specificities, these should not be construed as limitations on the scope of the invention, but rather as an exemplification of one embodiment thereof. Many other variations are possible. For example, an alternative embodiment of this invention would be one wherein the music could be generated instead of selecting sound files, allowing the salience, modulation, and variance protocols, as well as any 3D audio protocols, to be applied to the production the audio components themselves. FIG. 7 depicts such an embodiment using a synthesizer (750) which generates audio. The variance protocol (700) is used in the sound design (701), the salience protocol (710) effects (711) and 3D effects (720) are put on the effects rack (740). Finally, the modulation protocol (730) instructs a low frequency oscillator (731) which modulates the audio all within the synthesizer itself (750) to produce the final audio composition (760). This and other embodiments could be accomplished using modular synthesizer hardware rather than a computer. In another embodiment, modulation can be accomplished via expert timing of live performers, such that using the methods of this present invention, one could conceivably lull an audience to sleep using at least two instruments, some or all of which are modulated regularly by increasing and decreasing the volume of their instruments, either manually or using a pre-programmed amplifier that does the same.

Some embodiments of this invention include a sleep protocol whereby aspects of the audio composition, such as duration, salience, variability, and modulation, vary over time to assist with sleep or for secondary purposes. For example, in one embodiment, the audio composition may begin with a higher frequency of modulation, which over time descends to a frequency suitable for slow-wave sleep. In another embodiment, the audio composition may incorporate a higher degree of salience after a certain period of time in order to rouse the listener to wakefulness. In other embodiments, these aspects of the audio composition may be linked to biofeedback mechanisms to coordinate the playing of the audio composition with the listener's sleep state.

Accordingly, the scope of the invention should be determined not by the embodiment(s) illustrated, but by the appended claims and their legal equivalents.

The invention claimed is:

1. A method for producing an audio composition for use in improving the quality of sleep, comprising:
   a) selecting a variance protocol across a timeline of the audio composition, said variance protocol establishing at least one audio component to produce a variance level to prevent the brain from habituating;
   b) selecting a salience protocol across a timeline of the audio composition, said salience protocol establishing at least one audio component to produce low salience;
   c) selecting a modulation protocol across a timeline of the audio composition, said modulation protocol establishing at least one audio component to produce slow-wave frequencies;
   d) generating a plurality of audio components in accordance with said variance protocol, said salience protocol and said modulation protocol; and
   e) mixing said plurality of audio components to output a final audio composition.

2. The method according to claim 1, further comprising applying 3D audio spatial audio techniques to said plurality of audio components.

3. The method according to claim 1, wherein the modulation protocol, at least in part, establishes a frequency range of 0.1 to 3 hertz.

4. The method according to claim 1, further comprising selecting a sleep protocol, wherein the final audio composition is output as sound according to one or more prompts.

5. The method according to claim 4, wherein said one or more prompts include time, duration, state of sleep or wakefulness, stage of sleep, length of sleep, and slow-wave sleep.

6. The method according to claim 1, wherein said salience protocol includes at least one parameter of filtering, balancing, smooth transitions, limited high frequency sounds, consistent melodic structure, specific compositional choices, regularity of sound, consistency of complexity, limited repetitive sounds, and consistency of loudness.

7. The method according to claim 1, wherein said variance protocol includes at least one parameter of multiple frequency components, changes in music over time, long length of loop time, limited repetitive elements, elements that initially attract attention, and periodic introduction of novel stimuli.

8. The method according to claim 1, further comprising adding an audio component selected to wake or rouse a listener to wakefulness.

9. The method according to claim 1, further comprising producing said final audio composition as sound from one or more speakers.

10. The method according to claim 1, further comprising producing said final audio composition as sound from one or more headphones.

11. The method according to claim 1, further comprising transmitting said final audio composition to one or more recipients electronically.

12. A method for modifying an audio composition for use in improving the quality of sleep, comprising:
   a) selecting an audio composition comprising a plurality of audio components;
   b) selecting a variance protocol for application across a timeline of the audio composition, said variance protocol establishing at least one audio component of said plurality of audio components to produce a variance level to prevent the brain from habituating;
   c) selecting a salience protocol for application across a timeline of the audio composition, said salience protocol establishing parameters for at least one audio component of said plurality of audio components to produce low salience;
   d) selecting a modulation protocol for application across a timeline of the audio composition, said modulation protocol establishing at least one audio component of said plurality of audio components to produce slow-wave frequencies;
   e) applying said variance protocol, said salience protocol and said modulation protocol to said plurality of audio components; and
   f) mixing said plurality of audio components to output a final audio composition.

13. The method according to claim 12, further comprising applying 3D audio spatial audio techniques to said plurality of audio components.

14. The method according to claim 12, wherein the modulation protocol, at least in part, establishes a frequency range of 0.1 to 3 hertz.

15. The method according to claim 12, wherein at least one modulated audio component is synchronized with at least one other audio component of said plurality of audio components.

16. The method according to claim 12, further comprising selecting a sleep protocol, wherein the final audio composition is output as sound according to one or more prompts.

17. The method according to claim 12, wherein one or more audio compositions are stored on one or more electronic medium.

* * * * *